(12) United States Patent
LaBeaume

(10) Patent No.: US 9,703,192 B2
(45) Date of Patent: Jul. 11, 2017

(54) ONIUM COMPOUNDS AND METHODS OF SYNTHESIS THEREOF

(71) Applicant: Rohm and Haas Electronic Materials LLC, Marlborough, MA (US)

(72) Inventor: Paul J. LaBeaume, Auburn, MA (US)

(73) Assignee: Rohm and Haas Electronic Materials LLC, Marlborough, MA (US)

( * ) Notice: Subject to any disclaimer, the term of this patent is extended or adjusted under 35 U.S.C. 154(b) by 0 days.

(21) Appl. No.: 14/027,361

(22) Filed: Sep. 16, 2013

(65) Prior Publication Data

US 2014/0080056 A1    Mar. 20, 2014

Related U.S. Application Data

(60) Provisional application No. 61/701,612, filed on Sep. 15, 2012.

(51) Int. Cl.
| | | |
|---|---|---|
| G03F 7/004 | (2006.01) | |
| G03F 7/038 | (2006.01) | |
| G03F 7/039 | (2006.01) | |
| C07C 303/32 | (2006.01) | |

(52) U.S. Cl.
CPC .......... G03F 7/0045 (2013.01); C07C 303/32 (2013.01); G03F 7/0046 (2013.01); G03F 7/0382 (2013.01); G03F 7/0392 (2013.01); G03F 7/0397 (2013.01)

(58) Field of Classification Search
CPC .... C07C 303/32; C07C 309/12; C07D 335/16
See application file for complete search history.

(56) References Cited

U.S. PATENT DOCUMENTS

| | | | |
|---|---|---|---|
| 7,217,492 B2 | 5/2007 | Yoneda et al. | |
| 2005/0233253 A1 | 10/2005 | Ishihara et al. | |
| 2010/0055608 A1* | 3/2010 | Ohashi ................. | C07D 493/18 430/270.1 |
| 2012/0231392 A1 | 9/2012 | Yamaguchi et al. | |
| 2012/0237876 A1 | 9/2012 | Maruyama | |

FOREIGN PATENT DOCUMENTS

| | | |
|---|---|---|
| CN | 1622943 A | 6/2005 |
| CN | 101125823 A | 2/2008 |
| JP | 2008189601 A | 8/2008 |
| JP | 2009221195 A | 10/2009 |
| JP | 2012-167084 A | 9/2012 |
| JP | 5739497 B2 | 6/2015 |
| WO | 2003/074509 A1 | 9/2003 |
| WO | 03074509 A1 | 12/2003 |
| WO | 2011070947 A1 | 6/2011 |

OTHER PUBLICATIONS

Stadler et al., "Fluorescent DNA Nanotags Featuring Covalently Attached Intercalating Dyes: Synthesis, Antibody Conjugation, and Intracellular Imaging," Bioconjugate Chemistry, 2011, 22, 1491-1502.*
Daintith, John Martin, Elizabeth. (2010). Dictionary of Science (6th Edition)—onium ion. Oxford University Press.*
Robert, "Synthesis of selenols and selenides from thiols and sulfides," Sel. Org. React. Database (SORD), 2006, p. 1-248.*
Orlova et al., "Synthesis of Amphiphilic Thiatrimethinecyanines," Russian Journal of Organic Chemistry, vol. 40, No. 2, 2004, 228-231.*
Bates et al., "Diphosphiranium (P2C) or Diphosphetanium (P2C2) Cyclic Cations: Different Fates for the Electrophile-Initiated Cyclodimerization of a Phosphaalkene," J. Am. Chem. Soc., 2006, 128, 15998-15999 (S1-S4).*
English Language Summary of Office Action dated Oct. 23, 2015, issued in counterpart Korean Patent Application No. 10-2013-0111065 (2 Pages).
English Language Summary of Second Office Action issued in counterpart Chinese Patent Application No. 201310637227 (9 Pages).
Chinese Office Action and English summary thereof dated Mar. 9, 2015 for corresponding Application No. 201310637227.2.
English language summary of Taiwan Examination report dated Sep. 25, 2015 for corresponding Taiwan Application No. 102133124.
English language summary of Japanese Office action dated Jun. 25, 2015 for corresponding Japanese application No. 2013-190009.
Korean Office action dated Jan. 27, 2015 for corresponding Korean application No. 10-2013-0111065.
English Language Summary of Office Action issued in counterpart Japanese Patent Application No. 2015-209987 (7 Pages).
English Language Summary of Office Action issued in counterpart Japanese Patent Application No. 2013-190009 (14 Pages).
English Language Summary of Office Action issued in counterpart Chinese Patent Application No. 201310637227.2 (2 Pages).

* cited by examiner

*Primary Examiner* — Paul A Zucker
*Assistant Examiner* — Mark Luderer
(74) *Attorney, Agent, or Firm* — Mintz Levin Cohn Ferris Glovsky and Popeo, P.C.; Peter F. Corless

(57) ABSTRACT

New onium salt compounds and methods for synthesis of such compounds are provided. Preferred methods of the invention include (a) providing an onium salt compound comprising a sulfonate component having an electron withdrawing group; and (b) treating the onium salt compound with a halide salt to form a distinct salt of the onium compound. The present onium compounds are useful as an acid generator component of a photoresist composition.

23 Claims, No Drawings

ONIUM COMPOUNDS AND METHODS OF SYNTHESIS THEREOF

This Application claims the benefit of priority under 35 U.S.C. §119(e) to U.S. Provisional Application No. 61/701,612, filed Sep. 15, 2012, the entire contents of which application are incorporated herein by reference.

FIELD

The present invention relates to new onium salt compounds and methods for synthesis of such compounds. Onium compounds of the invention are useful as an acid generator component of a photoresist composition.

INTRODUCTION

Photoresists are photosensitive films for transfer of images to a substrate. They form negative or positive images. After coating a photoresist on a substrate, the coating is exposed through a patterned photomask to a source of activating energy such as ultraviolet light to form a latent image in the photoresist coating. The photomask has areas opaque and transparent to activating radiation that define an image desired to be transferred to the underlying substrate. A relief image is provided by development of the latent image pattern in the resist coating.

Photoresists typically contain a resin component and an acid generator compound component. Onium salt compounds have been utilized as a photoresist acid generator component. See U.S. Pat. No. 6,929,896; 2010/0143843; and 2012/0015297.

Known photoresists can provide features having resolution and dimension sufficient for many existing commercial applications. However for many other applications, the need exists for new photoresists that can provide highly resolved images of submicron dimension.

Various attempts have been made to alter the make-up of photoresist compositions to improve performance of functional properties. Among other things, a variety of photoactive compounds have been reported for use in photoresist compositions. See U.S. 20070224540 and EP 1906241. Extreme ultraviolet (EUV) and e-beam imaging technologies also have been employed. See U.S. Pat. No. 7,459,260. EUV utilizes short wavelength radiation, typically between 1 nm to 40 nm, with 13.5 nm radiation often employed.

It would be desirable to have improved photoresist compositions, including improved routes to photoresist photoactive components.

SUMMARY

We have now discovered new methods for synthesis of onium salt compounds. We also provide new onium salt acid generator compounds and photoresist composition comprising such acid generators.

Among other things, methods of the invention can provide convenient change of strong acid anion components of an onium salt compound to provide an onium compound with a distinct anion component.

More particularly, in one aspect, methods for preparing an onium salt compound are provided comprising: (a) providing an onium salt compound comprising a sulfonate component, wherein the sulfonate component comprises an electron withdrawing group; and (b) treating the onium salt compound with a halide salt to form a distinct salt of the onium compound.

In such methods, preferably the sulfonate anion component of the onium compound comprises one or more electron withdrawing groups on a carbon atom alpha to an $SO_3$-moiety. Suitable electron withdrawing groups include one or more halogen atoms (especially fluoro); cyano; nitro; and alkyl such as $C_{1-20}$alkyl substituted with one or more halogen (especially fluoro), nitro and/or cyano.

In the methods of the invention, the onium salt compound may be treated with varying halide salts such as Br, Cl and I salts, with iodide salts preferred.

The onium salt may be treated with a halide salt in a variety of ways, suitably to permit displacement of an anion component of the onium salt compound with the halide anion of the halide salt to thereby form the distinct salt of the onium compound. That is, the distinct salt of the onium compound will have a different anion component (e.g. halide such as $I^-$) than the anion component (e.g. triflate $(CF_3SO_3^-)$) of the provided onium salt compound.

In one suitable treatment method, the onium salt compound is washed with a fluid solution comprising the halide salt. Such washing may be suitably carried out in a variety of ways e.g. by admixing an organic solvent solution of the onium salt compound with an aqueous solution comprising the halide salt (e.g. 1, 2 or 3M aqueous solution of the halide salt) for a time and conditions (such as agitation or stirring) sufficient to form a distinct salt of the onium compound.

A desired distinct salt of the onium compound also may be formed through further processing following the halide salt treatment. For instance, a formed halide salt of the onium compound may undergo an additional anion displacement reaction to provide an onium salt compound that is distinct from both 1) the first onium salt compound provided for treatment with the halide salt, and 2) the halide salt formed from the first onium salt compound. In other words, the formed halide salt of the provided onium salt compound may function as an intermediate for synthesis of other onium salt compounds with differing anion components.

Methods of the invention may include treatment and forming of a variety of onium compounds, including those having sulfonium cation components as well as iodonium cation components. Suitable sulfonium cation components may include non-cyclic sulfonium moieties where the sulfonium atom $(S^+)$ may be substituted by non-aromatic (e.g. optionally substituted alkyl) and aromatic (e.g. optionally substituted phenyl or naphthyl), cyclic sulfonium moieties (e.g. aromatic or non-aromatic 5- or 6-member rings that comprise carbon ring atoms and at least one $S^+$ ring member), and/or thioxanthone moieties.

Additional suitable cation components of acid generators of the invention may include those of the following formula

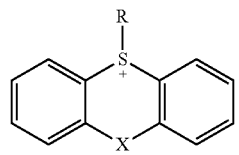

wherein in that formula X is C=O, S(O), $SO_2$, C(=O)O, C(=O)NH, C(=O)—C(=O)—, or —O—; and R is a non-hydrogen substituent such as optionally substituted carbocyclic aryl including phenyl and optionally substituted alkyl, including $C_{1-20}$ optionally substituted alkyl.

Photoresist compositions and methods for preparing photoresist compositions also are provided. Particularly preferred photoresists of the invention may comprise an imaging-effective amount of one or more onium salt compounds as disclosed herein and a suitable polymer component. Photoresists of the invention also may comprise a mixture of differing onium salt compounds, typically a mixture of 2 or 3 different onium salt compounds, more typically a mixture that consists of a total of 2 differing onium salt compounds.

In preferred aspects, onium salt compounds and photoresists of the invention are utilized for EUV imaging. Photoresists comprising one or more onium salt compounds as disclosed herein also may be imaged with other radiation sources such as 193 nm and e-beam radiation.

Methods are also provided for forming relief images of photoresist compositions of the invention (including patterned lines with sub sub-50 nm or sub-20 nm dimensions). Substrates such as a microelectronic wafer also are provided having coated thereon a photoresist composition of the invention.

DETAILED DESCRIPTION

We have found that prior onium salt syntheses can have certain limitations, including producing a triflate salt onium acid generator, where the triflate can be difficult to displace with another desired anion component. As discussed above, such shortcomings of prior approaches can be addressed by the present methods which can effectively replace a strong acid anion component of an onium salt compound as desired.

More particularly, we now provide new methods for methods for preparing onium salt compounds which comprise: (a) providing an onium salt compound comprising a sulfonate component, wherein the sulfonate component comprises an electron withdrawing group; and (b) treating the onium salt compound with a halide salt to form a distinct salt of the onium compound.

In certain aspects, the provided onium compound is a triflate salt (i.e. $CF_3SO_3^-$ anion component) and is treated with an iodide salt such as sodium iodide, potassium iodide or ammonium iodide. Suitable halide salt treatment of the onium compound can include contact with a fluid solution comprising the iodide salt. Preferably, the onium salt is contacted such as by washing multiple times (e.g., 2, 3, 4, 5 or more times) with an aqueous solution of the halide salt, although a single wash or other single exposure with the halide salt also may be employed. As discussed above, halide salt solutions of varying concentrations may be suitably employed, e.g. 1, 2, 3 or 4M aqueous solution of the halide salt. Treatment of the onium compound with a halide salt can be suitably conducted under relatively mild conditions, e.g. at room temperature (25° C.).

We have found that such halide anion treatment can displace strong acids such as triflate or other activated sulfonate from the onium cation component enabling formation of a distinct onium compound, i.e. the onium cation component complexed with a different anion component (e.g. different than the triflate anion of the provided onium compound).

We also found that use of an iodide salt can provide enhanced results relative to other salts evaluated for displacement of a strong acid anion component of an onium salt compound. Other salts evaluated included chloride, bromide and acetate salts. Thus, we found that iodide salt treatment of a triflate salt sulfonium compound resulted in enhanced displacement of the triflate anion relative to comparable treatment with chloride, bromide or acetate salts. Enhanced displacement included higher yield of a distinct sulfonium salt (i.e. distinct from the triflate salt) while using a comparatively reduced number of salt washing cycles.

As discussed above, in the present methods, preferred sulfonate anion components of the provided onium compound may comprise one or more electron withdrawing groups. Suitable electron withdrawing groups include one or more halogen atoms; cyano; nitro; and alkyl such as $C_{1-20}$alkyl substituted with one or more halogen (especially fluoro), nitro and/or cyano. Halogen particularly fluoro and $C_{1-20}$alkyl substituted with one or more halogen (especially fluoro) are often preferred. Preferred sulfonate components of the provided onium compound may comprise a triflate moiety as well as other fluorinated alkylsulfonate groups, such as alkylsulfonate having 1-20 carbons and 1-20 or more fluorine atoms, including perfluorinated alkylsulfonate groups.

In a preferred aspect, the sulfonate anion component of a provided onium compound is of the following general formula (I):

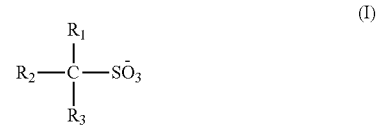

wherein $R_1$ and $R_3$ are independently selected from hydrogen, halogen, cyano, nitro, optionally substituted alkyl, and optionally substituted carbocyclic aryl; $R_2$ is the same or different than $R_1$ and $R_3$ and is selected from a linker moiety, hydrogen, halogen, cyano, nitro, optionally substituted alkyl, and optionally substituted carbocyclic aryl, and wherein at least one $R_1$, $R_2$ and $R_3$ is an electron withdrawing group. In preferred embodiments, one or more of $R_1$, $R_2$ and $R_3$ are halogen or halogenated alkyl, such as fluorine and fluorinated alkyl e.g. having 1 to 20 carbons and 1 to 20 or more fluorine atoms, including perfluorinated alkyl.

In a further preferred aspect, the anion component of a provided onium compound may be a sulfonate of the following general formula (II):

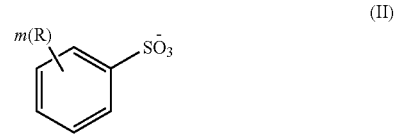

wherein in formula (II) each R is the same or different and is an electron-withdrawing group such as halogen, cyano, nitro, or a substituted alkyl; or other optionally substituted alkyl or optionally substituted carbocyclic aryl, with at least one R being an electron-withdrawing moiety; and m is an integer of from 1 to 5. In preferred embodiments, one or more R groups are halogen or halogenated alkyl, such as fluorine and fluorinated alkyl e.g. having 1 to 20 carbons and 1 to 20 or more fluorine atoms, including perfluorinated alkyl.

The present invention also provides onium salt compounds as may be suitably obtainable by methods disclosed herein.

More particularly, iodide salt onium compounds are provided, obtainable by methods comprising:

(a) providing an onium salt compound comprising a sulfonate component, wherein the sulfonate component comprises an electron withdrawing group; and (b) treating the onium salt compound with a halide salt to form a distinct salt of the onium compound Additional onium salt compounds also are provided, obtainable by methods comprising:

(a) providing an onium salt comprising a sulfonate component, wherein the sulfonate component an electron withdrawing group;

(b) treating the sulfonate salt with a halide salt to form a halide salt of the onium compound; and (c) treating the halide salt of the onium compound to form a distinct salt of the onium compound.

Photoresist Compositions

As discussed above, onium salt compounds as disclosed herein are useful as the radiation sensitive component in photoresist compositions, including both positive-acting and negative-acting chemically amplified resist compositions.

The photoresists of the invention typically comprise a polymer and one or more onium salt compound as disclosed herein that function as acid generators during lithographic processing. Preferably the polymer has functional groups that impart alkaline aqueous developability to the resist composition. For example, preferred are polymers that comprise polar functional groups such as hydroxyl or carboxylate, or acid-labile groups that can liberate such polar moieties upon lithographic processing. Preferably the polymer is used in a resist composition in an amount sufficient to render the resist developable with an aqueous alkaline solution.

Onium salt compounds of the invention are also suitably used with polymers that comprise repeat units containing aromatic groups, such as optionally substituted phenyl including phenol, optionally substituted naphthyl, and optionally substituted anthracene. Optionally substituted phenyl (including phenol) containing polymers are particularly suitable for many resist systems, including those imaged with EUV and e-beam radiation. For positive-acting resists, the polymer also preferably contains one or more repeat units that comprise acid-labile groups. For example, in the case of polymers containing optionally substituted phenyl or other aromatic groups, a polymer may comprise repeat units that contain one or more acid-labile moieties such as a polymer that is formed by polymerization of acrylate or methacrylate monomers that comprise an acid-labile ester (e.g. t-butyl acrylate or methacrylate). Such monomers may be copolymerized with one or more other monomers that comprise aromatic group(s) such as optionally phenyl, e.g. a styrene or vinyl phenol monomer.

Preferred monomers used for the formation of such polymers include: an acid-deprotectable monomer having the formula (V), a lactone-containing monomer of the formula (VI), a base-soluble monomer of formula (VII) for adjusting dissolution rate in alkaline developer, and an acid-generating monomer of the formula (VIII), or a combination comprising at least one of the foregoing monomers:

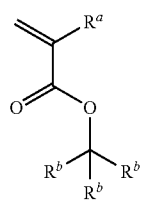

(V)

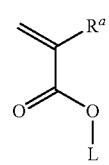

(VI)

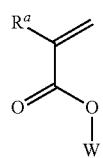

(VII)

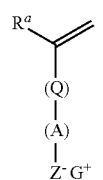

(VIII)

wherein each $R^a$ is independently H, F, —CN, $C_{1-10}$ alkyl, or $C_{1-10}$ fluoroalkyl. In the acid-deprotectable monomer of formula (V), $R^b$ is independently $C_{1-20}$ alkyl, $C_{3-20}$ cycloalkyl, $C_{6-20}$ aryl, or $C_{7-20}$ aralkyl, and each $R^b$ is separate or at least one $R^b$ is bonded to an adjacent $R^b$ to form a cyclic structure. In lactone-containing monomer of formula (VI), L is a monocyclic, polycyclic, or fused polycyclic $C_{4-20}$ lactone-containing group. In the base solubilizing monomer of formula (VII), W is a halogenated or non-halogenated, aromatic or non-aromatic $C_{2-50}$ hydroxyl-containing organic group having a pKa of less than or equal to 12. In the acid generating monomer of formula (VIII), Q is ester-containing or non-ester containing and fluorinated or non-fluorinated and is $C_{1-20}$ alkyl, $C_{3-20}$ cycloalkyl, $C_{6-20}$ aryl, or $C_{7-20}$ aralkyl group, A is ester-containing or non-ester-containing and fluorinated or non-fluorinated, and is $C_{1-20}$ alkyl, $C_{3-20}$ cycloalkyl, $C_{6-20}$ aryl, or $C_{7-20}$ aralkyl, $Z^-$ is an anionic moiety comprising carboxylate, sulfonate, an anion of a sulfonamide, or an anion of a sulfonimide, and $G^+$ is a sulfonium or iodonium cation.

Exemplary acid-deprotectable monomers include but are not limited to:

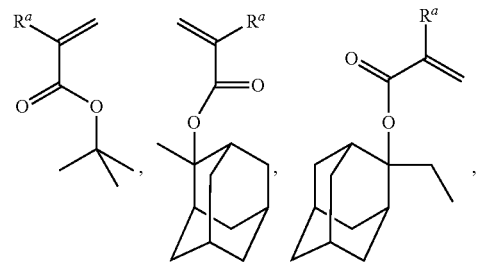

-continued

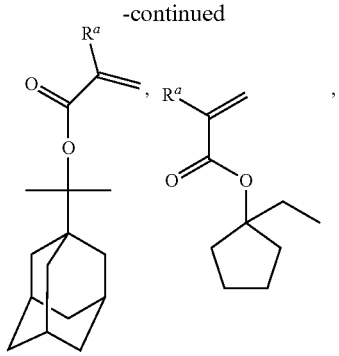

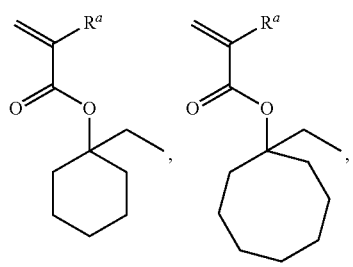

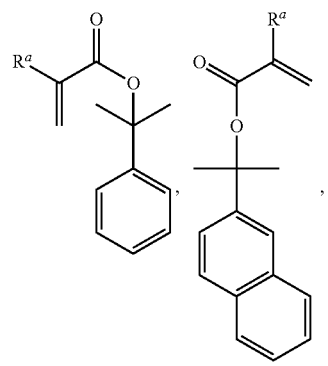

or a combination comprising at least one of the foregoing, wherein $R^a$ is H, F, —CN, $C_{1-6}$ alkyl, or $C_{1-6}$ fluoroalkyl.

Suitable lactone monomers may be of the following formula (IX):

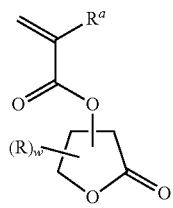

(IX)

wherein $R^a$ is H, F, —CN, $C_{1-6}$ alkyl, or $C_{1-6}$ fluoroalkyl, R is a $C_{1-10}$ alkyl, cycloalkyl, or heterocycloalkyl, and w is an integer of 0 to 5. In formula (IX), R is attached directly to the lactone ring or commonly attached to the lactone ring and/or one or more R groups, and the ester moiety is attached to the lactone ring directly, or indirectly through R.

Exemplary lactone-containing monomers include:

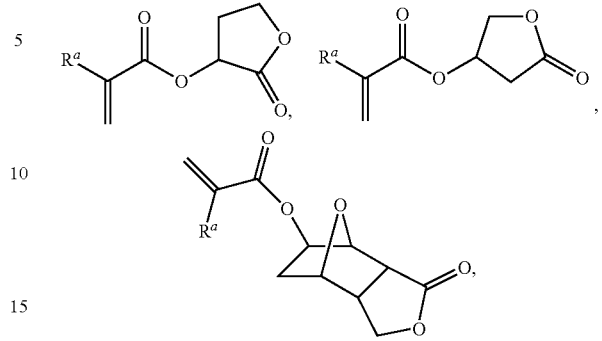

or a combination comprising at least one of the foregoing monomers, wherein $R^a$ is H, F, —CN, $C_{1-10}$ alkyl, or $C_{1-10}$ fluoroalkyl.

Suitable base-soluble monomers may be of the following formula (X):

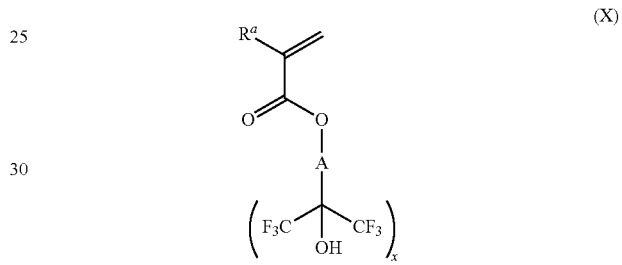

(X)

wherein each $R^a$ is independently H, F, —CN, $C_{1-10}$ alkyl, or $C_{1-10}$ fluoroalkyl, A is a hydroxyl-containing or non-hydroxyl containing, ester-containing or non ester-containing, fluorinated or non-fluorinated $C_{1-20}$ alkylene, $C_{3-20}$ cycloalkylene, $C_{6-20}$ arylene, or $C_{7-20}$ aralkylene, and x is an integer of from 0 to 4, wherein when x is 0, A is a hydroxyl-containing $C_{6-20}$ arylene.

Exemplary base soluble monomers include those having the following structures:

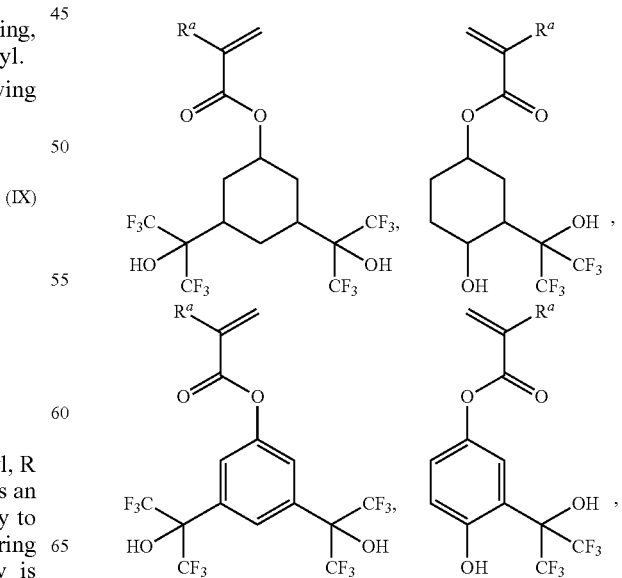

-continued

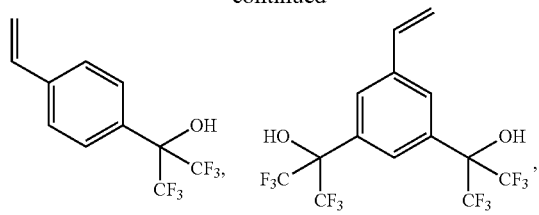

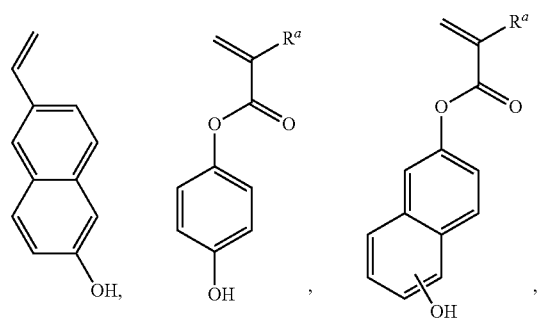

or a combination comprising at least one of the foregoing, wherein $R^a$ is H, F, —CN, $C_{1-6}$ alkyl, or $C_{1-6}$ fluoroalkyl.

Preferred acid generating monomer include those of the formulae (XI) or (XII):

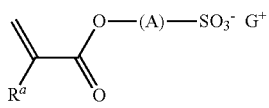
(XI)

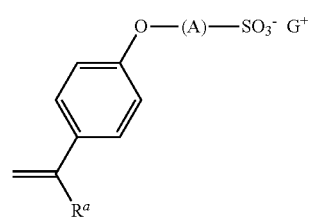
(XII)

wherein each $R^a$ is independently H, F, —CN, $C_{1-6}$ alkyl, or $C_{1-6}$ fluoroalkyl, A is a fluorine-substituted $C_{1-30}$ alkylene group, a fluorine-substituted $C_{3-30}$ cycloalkylene group, a fluorine-substituted $C_{6-30}$ arylene group, or a fluorine-substituted $C_{7-30}$ alkylene-arylene group, and $G^+$ is a sulfonium or iodonium cation.

Preferably, in formulas (XI) and (XII), A is a —[C(R$^1$)$_2$]$_x$C(=O)O]$_b$—C((R$^2$)$_2$)$_y$(CF$_2$)$_z$— group, or an o-, m- or p-substituted-C$_6$F$_4$— group, where each R$^1$ and R$^2$ are each independently H, F, —CN, $C_{1-6}$ fluoroalkyl, or $C_{1-6}$ alkyl, b is 0 or 1, x is an integer of 1 to 10, y and z are independently integers of from 0 to 10, and the sum of y+z is at least 1.

Exemplary preferred acid generating monomers include:

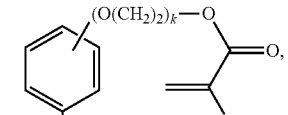
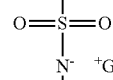
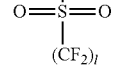
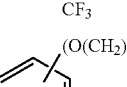
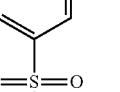
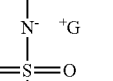
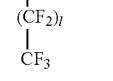
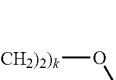
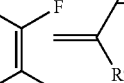
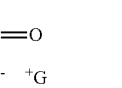
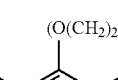
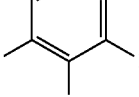
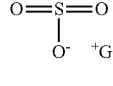
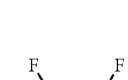
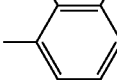
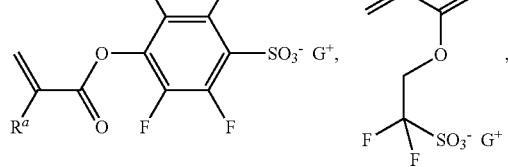
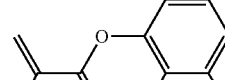
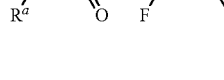
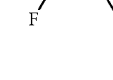

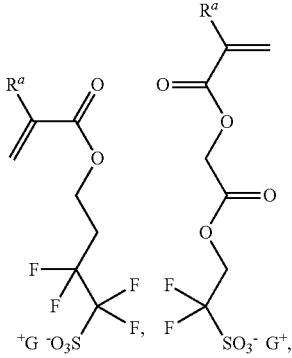

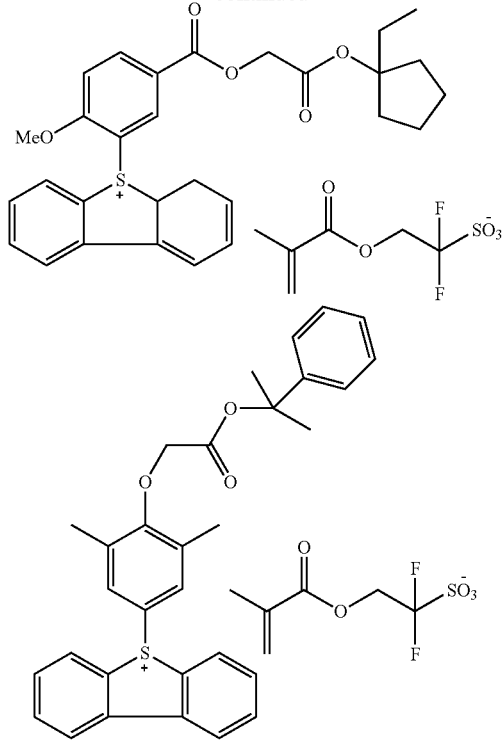

or a combination comprising at least one of the foregoing, where each $R^a$ is independently H, F, —CN, $C_{1-6}$ alkyl, or $C_{1-6}$ fluoroalkyl, k is suitably an integer of from 0 to 5; and $G^+$ is a sulfonium or iodonium cation.

Preferred acid-generating monomers may include sulfonium or iodonium cation. Preferably, in formula (IV), $G^+$ is of the formula (XIII):

(XIII)

wherein X is S or I, each $R^0$ is halogenated or non-halogenated and is independently $C_{1-30}$ alkyl group; a polycyclic or monocyclic $C_{3-30}$ cycloalkyl group; a polycyclic or monocyclic $C_{4-30}$ aryl group; or a combination comprising at least one of the foregoing, wherein when X is S, one of the $R^0$ groups is optionally attached to one adjacent $R^0$ group by a single bond, and a is 2 or 3, wherein when X is I, a is 2, or when X is S, a is 3.

Exemplary acid generating monomers include those having the formulas:

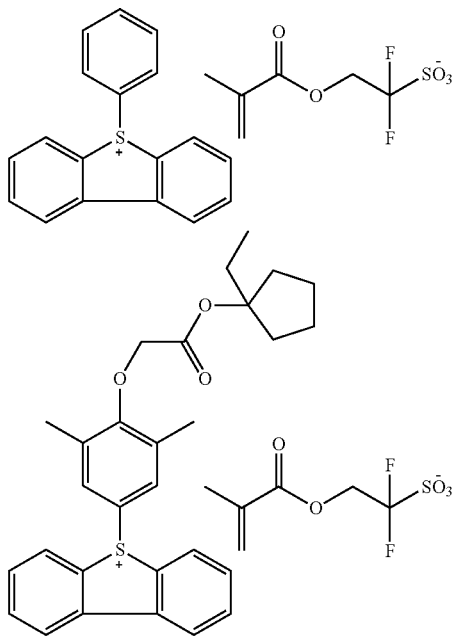

wherein $R^a$ is H, F, —CN, $C_{1-6}$ alkyl, or $C_{1-6}$ fluoroalkyl.

Suitable polymers that have acid-labile deblocking groups for use in positive-acting chemically amplified photoresists of the invention also have been disclosed in European Patent Application 0829766A2 (polymers with acetal and ketal polymers) and European Patent Application EP0783136A2 (terpolymers and other copolymers including units of 1) styrene, 2) hydroxystyrene, and 3) acid labile groups, particularly alkyl acrylate acid labile groups such as polymerized t-butylmethacrylate and methyladamantylmethacrylate.

Polymers for use in photoresists of the invention may suitably vary widely in molecular weight and polydisperity. Suitable polymers include those that have a M, of from about 1,000 to about 50,000, more typically about 2,000 to about 30,000 with a molecular weight distribution of about 3 or less, more typically a molecular weight distribution of about 2 or less.

Preferred negative-acting compositions of the invention comprise a mixture of materials that will cure, crosslink or harden upon exposure to acid, and a photoactive component of the invention. Preferred negative acting compositions comprise a polymer binder such as a phenolic or non-aromatic polymer, a crosslinker component and a photoactive component of the invention. Such compositions and the use thereof have been disclosed in European Patent Applications 0164248 and U.S. Pat. No. 5,128,232 to Thackeray et al. Preferred phenolic polymers for use as the polymer binder component include novolaks and poly(vinylphenol)s such as those discussed above. Preferred crosslinkers include amine-based materials, including melamine, glycolurils, benzoguanamine-based materials and urea-based materials. Melamine-formaldehyde polymers are often particularly suitable. Such crosslinkers are commercially available, e.g. the melamine polymers, glycoluril polymers, urea-based polymer and benzoguanamine polymers, such as those sold by Cytec under tradenames Cymel 301, 303, 1170, 1171, 1172, 1123 and 1125 and Beetle 60, 65 and 80.

For imaging at 193 nm, suitable polymer components may be substantially free of aromatic content, e.g. less than 20, 10, 5 or 1 percent of total repeat units of the polymer used in the resist containing phenyl or other aromatic groups. See U.S. Pat. Nos. 7,208,261 and 7,968,268 for exemplary suitable photoresist compositions for imaging with 193 nm radiation.

Photoresists of the invention also may contain other materials. For example, other optional additives include actinic and contrast dyes, anti-striation agents, plasticizers, speed enhancers, sensitizers, photodestroyable bases etc. Such optional additives typically will be present in minor concentration in a photoresist composition.

Inclusion of base materials, preferably the carboxylate or sulfonate salts of photo-decomposable cations, provides a mechanism for neutralization of acid from the acid decomposable groups, and limits the diffusion of the radiation-generated acid, to thereby provide improved contrast in the photoresist.

Photo-destroyable bases include photo-decomposable cations, and preferably those also useful for preparing PAGs, paired with an anion of a weak (pKa>2) acid such as, for example, a $C_{1-20}$ carboxylic acid. Exemplary such carboxylic acids include formic acid, acetic acid, propionic acid, tartaric acid, succinic acid, cyclohexylcarboxylic acid, benzoic acid, salicylic acid, and other such carboxylic acids.

Alternatively, or in addition, other additives may include quenchers that are non-photo-destroyable bases, such as, for example, those based on hydroxides, carboxylates, amines, imines, and amides. Preferably, such quenchers include $C_{1-30}$ organic amines, imines, or amides, or may be a $C_{1-30}$ quaternary ammonium salt of a strong base (e.g., a hydroxide or alkoxide) or a weak base (e.g., a carboxylate). Exemplary quenchers include amines such as tripropylamine, dodecylamine, 1,1',1",1'''-(ethane-1,2-diylbis(azanetriyl))tetrapropan-2-ol; aryl amines such as diphenylamine, triphenylamine, aminophenol, and 2-(4-aminophenyl)-2-(4-hydroxyphenyl)propane, Troger's base, a hindered amine such as diazabicycloundecene (DBU) or diazabicyclononene (DBN), or ionic quenchers including quaternary alkyl ammonium salts such as tetrabutylammonium hydroxide (TBAH) or tetrabutylammonium lactate.

Surfactants include fluorinated and non-fluorinated surfactants, and are preferably non-ionic. Exemplary fluorinated non-ionic surfactants include perfluoro $C_4$ surfactants such as FC-4430 and FC-4432 surfactants, available from 3M Corporation; and fluorodiols such as POLYFOX PF-636, PF-6320, PF-656, and PF-6520 fluorosurfactants from Omnova.

The photoresist further includes a solvent generally suitable for dissolving, dispensing, and coating the components used in a photoresists. Exemplary solvents include anisole, alcohols including ethyl lactate, 1-methoxy-2-propanol, and 1-ethoxy-2 propanol, esters including n-butylacetate, 1-methoxy-2-propyl acetate, methoxyethoxypropionate, ethoxyethoxypropionate, ketones including cyclohexanone and 2-heptanone, and a combination comprising at least one of the foregoing solvents.

Such photoresists may include a polymer component in an amount of 50 to 99 wt %, specifically 55 to 95 wt %, more specifically 60 to 90 wt %, and still more specifically 65 to 90 based on the total weight of solids. The photo-destroyable base may be present in the photoresist in an amount of 0.01 to 5 wt %, specifically 0.1 to 4 wt %, and still more specifically 0.2 to 3 wt %, based on the total weight of solids. A surfactant may be included in an amount of 0.01 to 5 wt %, specifically 0.1 to 4 wt %, and still more specifically 0.2 to 3 wt %, based on the total weight of solids. A quencher may be included in relatively small amounts of for example, from 0.03 to 5 wt % based on the total weight of solids. Other additives may be included in amounts of less than or equal to 30 wt %, specifically less than or equal to 20%, or more specifically less than or equal to 10%, based on the total weight of solids. The total solids content for the photoresist composition may be 0.5 to 50 wt %, specifically 1 to 45 wt %, more specifically 2 to 40 wt %, and still more specifically 5 to 30 wt %, based on the total weight of solids and solvent. The acid generator compound(s) should be present in an amount sufficient to enable generation of a latent image in a coating layer of the resist. More specifically, the one or more onium compounds will suitably be present in an amount of from about 1 to 50 weight percent of total solids of a resist. It will be understood that the solids includes polymer, photo-destroyable base, quencher, surfactant, onium salt compound, and any optional additives, exclusive of solvent.

A coated substrate may be formed from the photoresist containing onium salt compounds(s) which should be present in an amount sufficient to enable generation of a latent image in a coating layer of the resist and onium salt compound(s). Such a coated substrate includes: (a) a substrate having one or more layers to be patterned on a surface thereof; and (b) a layer of the photoresist composition including the acid generator compound over the one or more layers to be patterned. For EUV or e beam imaging, photoresists may suitably have relatively higher content of onium salt compound(s), e.g. where the one or more onium salt compounds comprise 5 to 10 to about 50 weight percent of total solids of the resist. Typically, lesser amounts of the photoactive component will be suitable for chemically amplified resists.

The photoresists of the invention are generally prepared following known procedures with the exception that one or more one salt compounds of the invention are substituted for prior photoactive compounds used in the formulation of such photoresists. The photoresists of the invention can be used in accordance with known procedures.

Substrates may be any dimension and shape, and are preferably those useful for photolithography, such as silicon, silicon dioxide, silicon-on-insulator (SOI), strained silicon, gallium arsenide, coated substrates including those coated with silicon nitride, silicon oxynitride, titanium nitride, tantalum nitride, ultrathin gate oxides such as hafnium oxide, metal or metal coated substrates including those coated with titanium, tantalum, copper, aluminum, tungsten, alloys thereof, and combinations thereof. Preferably, the surfaces of substrates herein include critical dimension layers to be patterned including, for example, one or more gate-level layers or other critical dimension layer on the substrates for semiconductor manufacture. Such substrates may preferably include silicon, SOI, strained silicon, and other such substrate materials, formed as circular wafers having dimensions such as, for example, 20 cm, 30 cm, or larger in diameter, or other dimensions useful for wafer fabrication production.

Further, a method of forming an electronic device includes (a) applying a layer of a photoresist composition including on a surface of the substrate; (b) patternwise exposing the photoresist composition layer to activating radiation; and (c) developing the exposed photoresist composition layer to provide a resist relief image.

Applying may be accomplished by any suitable method, including spin coating, spray coating, dip coating, doctor blading, or the like. Applying the layer of photoresist is preferably accomplished by spin-coating the photoresist in solvent using a coating track, in which the photoresist is dispensed on a spinning wafer. During dispense, the wafer may be spun at a speed of up to 4,000 rpm, preferably from about 500 to 3,000 rpm, and more preferably 1,000 to 2,500 rpm. The coated wafer is spun to remove solvent, and baked on a hot plate to remove residual solvent and free volume from the film to make it uniformly dense.

Patternwise exposure is then carried out using an exposure tool such as a stepper, in which the film is irradiated through a pattern mask and thereby is exposed pattern-wise. The method preferably uses advanced exposure tools generating activating radiation at wavelengths capable of high resolution including extreme-ultraviolet (EUV) or e-beam radiation. Other radiation sources such as 193 nm radiation also may be used. It will be appreciated that exposure using the activating radiation decomposes the onium salt compound(s) in the exposed areas and generates acid and decomposition by-products, and that the acid then effects a chemical change in the polymer (deblocking the acid sensitive group to generate a base-soluble group, or alternatively, catalyzing a cross-linking reaction in the exposed areas). The resolution of such exposure tools may be less than 30 nm.

Developing the exposed photoresist layer is then accomplished by treating the exposed layer to a suitable developer capable of selectively removing the exposed portions of the film (where the photoresist is positive tone) or removing the unexposed portions of the film (where the photoresist is crosslinkable in the exposed regions, i.e., negative tone). Preferably, the photoresist is positive tone based on a polymer having acid sensitive (deprotectable) groups, and the developer is preferably a metal-ion free tetraalkylammonium hydroxide solution, such as, for example, aqueous 0.26 N tetramethylammonium hydroxide. A pattern forms by developing.

Additionally, for positive resists, unexposed regions can be selectively removed by treatment with a suitable nonpolar solvent for negative tone development. See U.S. 2011/0294069 for suitable procedures for negative tone development of positive photoresists. Typical nonpolar solvents for negative tone development are organic developers, such as a solvent chosen from ketones, esters, hydrocarbons, and mixtures thereof, e.g. acetone, 2-hexanone, methyl acetate, butyl acetate, and terahydrofuran.

The photoresist may, when used in one or more such a pattern-forming processes, be used to fabricate electronic and optoelectronic devices such as memory devices, processor chips (CPU's), graphics chips, and other such devices.

Examples 1-4

Syntheses of Onium Salt Compounds

Example 1

Synthesis of 10-(5-((2-(1-ethylcyclopentyloxy)-2-oxoethoxy)carbonyl)-2-methoxyphenyl)-9-oxo-9,10-dihydrothioxanthylium iodide

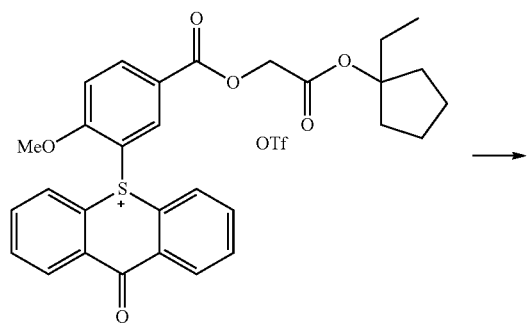

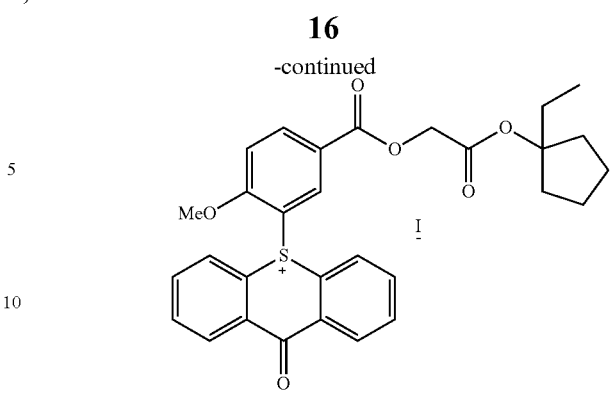

10-(5-((2-(1-ethylcyclopentyloxy)-2-oxoethoxy)carbonyl)-2-methoxyphenyl)-9-oxo-2-(trifluoromethyl)-4,4-a,9,10-tetrahydrothioxanthylium trifluoromethanesulfonate (20.9 g, 31.3 mmol) was dissolved in dichloromethane (250 mL), washed with 1M aqueous sodium iodide (4×250 mL), water (4×250 mL), dried ($Na_2SO_4$) and concentrated to afford the title compound (17.1 g, 84%) as a light orange solid. NMR (300 MHz, $(CD_3)_2SO$) δ: 9.05 (vis s, 1H), 8.52-8.59 (m, 2H), 8.35-8.43 (m, 1H), 8.20-8.28 (m, 2H), 7.93-8.08 (m, 4H), 7.35 (d, J=10 Hz, 1H), 4.91 (s, 2H), 3.47 (s, 3H), 1.90-2.10 (m, 4H), 1.5-1.73 (m, 6H), 0.89 (t, J=7 Hz, 3H).

Example 2

Synthesis of 10-(5-((2-(1-ethylcyclopentyloxy)-2-oxoethoxy)carbonyl)-2-methoxyphenyl)-9-oxo-4,4-a,9,10-tetrahydrothioxanthylium 3-hydroxyadamantane-acetoxy-1,1,2,2-tetrafluorobutane-1-sulfonate

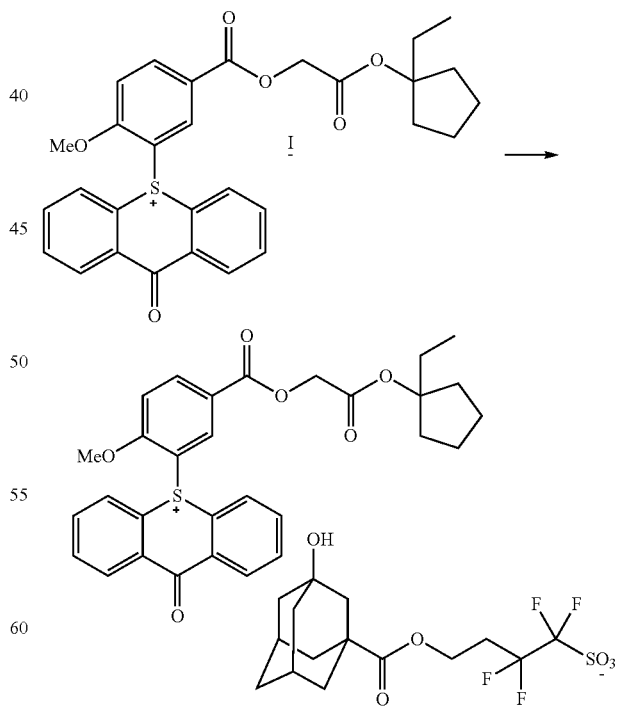

10-(5-((2-(1-ethylcyclopentyloxy)-2-oxoethoxy)carbonyl)-2-methoxyphenyl)-9-oxo-4,4-a,9,10-tetrahydrothioxanthylium iodide (5.00 g, 7.73 mmol) and 3-hydroxyadamantaneacetoxy-1,1,2,2-tetrafluorobutane-1-sulfonate sodium salt (3.46 g, 8.12 mmol) were dissolved in dichloromethane (125 mL) and water (125 mL) and stirred at r.t. overnight. The layers were separated and the aqueous phase washed with dichloromethane (3×100 mL). The combined organic layers were washed with water (4×250 mL) and concentrated to afford the title compound (5.56 g, 96%) as a light orange solid. NMR (300 MHz, (CD$_3$)$_2$SO) δ: 9.04 (vis s, 1H), 8.51-8.59 (m, 2H), 8.39 (dd, J=10, 2.4 Hz, 1H), 8.21-8.27 (m, 2H), 7.92-8.06 (m, 4H), 7.35 (d, J=10 Hz, 1H), 4.91 (s, 2H), 4.57 (s, 10H), 4.23 (t, J=6 Hz, 2H), 3.47 (s, 3H), 2.43-2.63 (m, 4H), 1.90-2.12 (m, 7H), 1.44-1.73 (m, 15H), 0.88 (t, J=7 Hz, 3H).

Example 3

Synthesis of 10-(5-((2-(1-ethylcyclopentyloxy)-2-oxoethoxy)carbonyl)-2-methoxyphenyl)-9-oxo-2-(trifluoromethyl)-9,10-dihydrothioxanthylium iodide

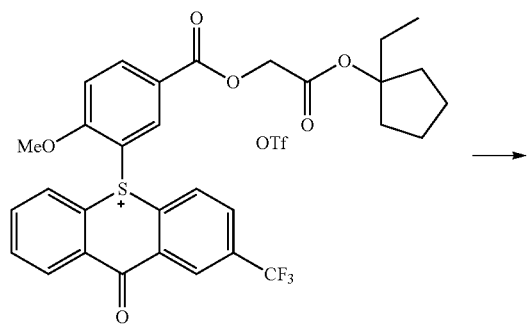

10-(5-((2-(1-ethylcyclopentyloxy)-2-oxoethoxy)carbonyl)-2-methoxyphenyl)-9-oxo-2-(trifluoromethyl)-4,4-a,9,10-tetrahydrothioxanthylium (5.21 g, 7.07 mmol) was dissolved in dichloromethane (100 mL) and washed with 1M aqueous sodium iodide (4×150 mL), water (4×150 mL), dried (Na$_2$SO$_4$) and concentrated to afford the title compound (3.81 g, 75%) as a light orange solid. NMR (500 MHz, (CD$_3$)$_2$SO) □: 9.17 (vis s, 1H), 8.73 (vis s, 1H), 8.55-8.59 (m, 1H), 8.47-8.52 (m, 1H), 8.37-8.43 (m, 2H), 8.23 (d, J=8.5 Hz, 1H), 7.98-8.07 (m, 2H), 7.35 (d, J=8.5 Hz, 2H).

Example 4

Synthesis of 10-(5-((2-(1-ethylcyclopentyloxy)-2-oxoethoxy)carbonyl)-2-methoxyphenyl)-9-oxo-2-(trifluoromethyl)-4,4-a,9,10-tetrahydrothioxanthylium 3-hydroxyadamantane-acetoxy-1,1,2,2-tetrafluorobutane-1-sulfonate

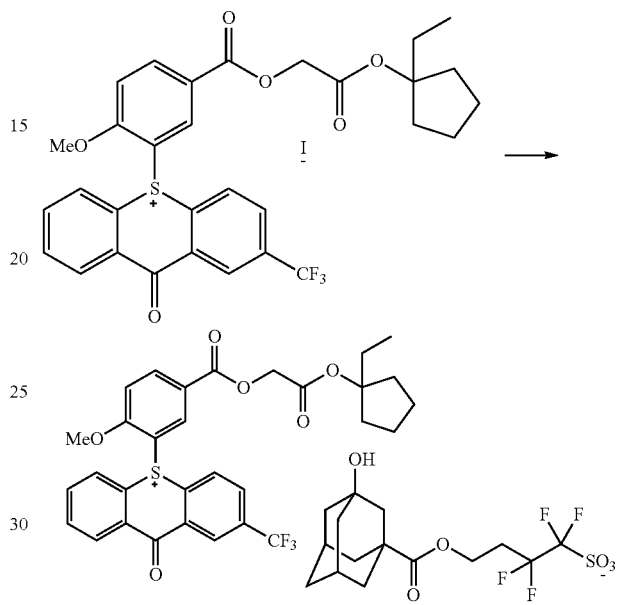

10-(5-((2-(1-ethylcyclopentyloxy)-2-oxoethoxy)carbonyl)-2-methoxyphenyl)-9-oxo-2-(trifluoromethyl)-4,4-a,9,10-tetrahydrothioxanthylium iodide (0.8 g, 1.12 mmol) and 3-hydroxyadamantane-acetoxy-1,1,2,2-tetrafluorobutane-1-sulfonate sodium salt (0.501 g, 1.18 mmol) were dissolved in dichloromethane (25 mL) and water (25 mL) and stirred at r.t. overnight. The layers were separated and the aqueous phase washed with dichloromethane (3×50 mL). The combined organic layers were washed with water (4×50 mL) and concentrated to afford the title compound (1.04 g, 95%) as a light orange solid. NMR (300 MHz, (CD$_3$)$_2$SO) δ: 9.21 (vis s, 1H), 8.73-8.78 (m, 1H), 8.37-8.61 (m, 6H), 8.21-8.26 (m, 1H), 7.97-8.08 (m, 2H), 7.35 (d, J=10 Hz, 1H, 4.94 (s, 2H), 4.24 (t, J=6 Hz, 2H), 3.45 (s, 3H), 2.44-2.63 (m, 4H), 1.89-2.12 (m, 7H), 1.44-1.74 (m, 15H), 0.88 (t, J=7 Hz, 3H).

Example 5

Preparation of Polymer with Acid Generator Units

Initiator solution was prepared by dissolving 65.96 g initiator (V-65) in 66 g acetonitrile/tetrahydrofuran (2/1 v/v). The polymerization was carried out in a 2 L 3-neck round bottom flask fitted with a water condenser and a thermometer to monitor the reaction in the flask. The contents were stirred using an overhead stirrer. The reactor was charged with the heel solution and the contents were heated to 75° C. The feed solution and the initiator solution were fed into the reactor using syringe pump over a 4 hour time period. The contents were then stirred for additional 2 hours, whereby, the reaction was quenched using hydroquinone (2.0 g). The contents were cooled to room temperature and precipitated twice out of 10× (by weight) IPE/MeOH 95/5 (w/w). The polymer obtained was dried in vacuuo after each precipitation step at 50° C. for 24 hours to yield 500 g polymer.

Example 6

Preparation and Processing of Photoresist Composition

A positive-tone photoresist composition is prepared by combining 21.088 g of a 10 wt % solution of the polymer from Example 20 in ethyl lactate, 18.779 g of a 2 wt % solution of the acid generator compound of Example 1 above in ethyl lactate, 1.898 g of a 0.5 wt % solution of 1,1',1'',1'''-(ethane-1,2-diylbis(azanetriyl))tetrapropan-2-ol in ethyl lactate, 0.422 g of a 0.5 wt % solution of fluorinated surfactant (Omnova PF656) in ethyl lactate, 47.342 g of ethyl lactate and 29.250 g of 2-hydroxyisobutyric acid methyl ester. The formulated resist is passed through a 0.01 μm PTFE filter. The thus prepared resist is spin coated onto a silicon wafer, soft baked to remove carrier solvent and exposed through a photomask to EUV radiation. The imaged resist layer is then baked at 110° C. for 60 seconds and then developed with an aqueous alkaline composition.

Example 7

Further Preparation and Processing of Photoresist Composition

A positive-tone photoresist composition is prepared by combining 21.088 g of a 10 wt % solution of the polymer from Example 20 in ethyl lactate, 19.522 g of a 2 wt % solution of the acid generator compound of Example 2 above in ethyl lactate, 1.898 g of a 0.5 wt % solution of 1,1',1'',1'''-(ethane-1,2-diylbis(azanetriyl))tetrapropan-2-ol in ethyl lactate, 0.422 g of a 0.5 wt % solution of fluorinated surfactant (Omnova PF656) in ethyl lactate, 46.342 g of ethyl lactate and 29.150 g of 2-hydroxyisobutyric acid methyl ester. The formulated resist is passed through a 0.01 μm PTFE filter. The thus prepared resist is spin coated onto a silicon wafer, soft baked to remove carrier solvent and exposed through a photomask to EUV radiation. The imaged resist layer is then baked at 110° C. for 60 seconds and then developed with an aqueous alkaline composition.

What is claimed is:

1. A method for preparing an onium salt compound for use as an acid generator, the method comprising:
   (a) providing an onium salt compound for use as an acid generator comprising a sultanate component, wherein the sulfonate component comprises an electron withdrawing group; and
   (b) washing the onium salt compound with a fluid composition comprising a halide salt to form a distinct salt of the onium compound; and
   (c) admixing the distinct salt of the onium compound with a polymer to provide a photoresist composition.

2. The method of claim 1 wherein the one or more electron withdrawing groups comprise one or more halogen atoms.

3. The method of claim 1 wherein the sulfonate component is a triflate.

4. The method of claim 1 wherein the sulfonate component is of the following general formula (I);

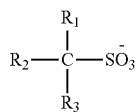

wherein $R_1$ and $R_3$ are independently selected from hydrogen, halogen, cyano, nitro, optionally substituted alkyl, and optionally substituted carbocyclic aryl;
$R_2$ is the same or different than $R_1$ and $R_3$ and is selected from a linker moiety, hydrogen, halogen, cyano, nitro, optionally substituted alkyl, and optionally substituted carbocyclic aryl,
wherein at least one $R_1$, $R_2$ and $R_3$ is an electron withdrawing group.

5. The method of claim 4 wherein (i) the onium salt compound is treated with a halide salt of the onium compound and (ii) the halide alt of the onium compound is treated to provide the distinct salt of the onium compound.

6. The method of claim 5 wherein one or more of $R_1$, $R_2$ and $R_3$ are halogen or halogenated alkyl.

7. The method of claim 1 wherein the sulfonate component is of the following general formula (II):

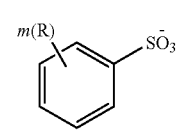

wherein each R is the same or different and is an electron-withdrawing group, optionally substituted alkyl, or optionally substituted carbocyclic aryl, with at least one R being an electron-withdrawing moiety; and m is an integer of from 1 to 5.

8. The method of claim 7 wherein R is halogen or halogenated alkyl.

9. The method of claim 1 wherein the onium salt compound is treated with an iodide salt to form a distinct salt of the onium compound.

10. The method of claim 9 wherein the onium salt compound is washed with a fluid solution of the iodide salt.

11. The method of claim 1 wherein the onium salt compound is a sulfonium compound.

12. The method of claim 11 wherein a sulfonium cation component of the sulfonium compound comprises a non-cyclic sulfonium moiety with a sulfonium atom substituted by non-aromatic or aromatic groups.

13. The method of claim 11 wherein a sulfonium cation component of the sulfonium compound comprises a cyclic sulfonium moiety.

14. The method of claim 11 wherein a sulfonium cation component of the sulfonium compound comprises a thioxanthone group.

15. The method of claim 11 wherein a sulfonium cation component of the sulfonium compound comprises a moiety of the following formula:

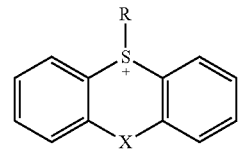

wherein X is C=O, S(O), $SO_2$, C(=O)O, C(=O)NH, C(=O)—C(=O)—, or —O—; and R is a non-hydrogen substituent.

16. The method of claim 1 wherein the onium salt compound is an iodonium compound.

17. A method for preparing an onium salt compound, the method comprising:

(a) providing a sulfonium salt compound comprising a sulfonate component, wherein the sulfonate component comprises an electron withdrawing group; and
(b) treating the sulfonium salt compound with a halide salt to permit displacement of the sulfonate component with the halide salt anion to provide a distinct salt of the onium compound.

18. The method of claim 17 wherein treating the onium salt with a halide salt provides a halide salt of the onium compound which undergoes an anion displacement reaction to provide the distinct salt of the onium compound.

19. The method of claim 18 further comprising admixing the distinct salt of the onium compound with a polymer to provide a photoresist composition.

20. A method for preparing an onium salt compound, the method comprising:
(a) providing a sulfonium salt compound comprising a sulfonate component, wherein 1) the sulfonate component comprises an electron withdrawing group and 2) a sulfonium cation component of the sulfonium compound comprises a cyclic sulfonium moiety; and
(b) treating the sulfonium salt compound with a halide salt to form a distinct salt of the onium compound.

21. The method of claim 20 wherein a sulfonium cation component of the sulfonium compound comprises a thioxanthone group.

22. The method of claim 20 wherein a sulfonium cation component of the sulfonium compound comprises a moiety of the following formula:

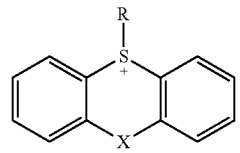

wherein X is C=O, S(O), SO$_2$, C(=O)O, C(=O)NH, C(=O)—C(=O)—, or —O—; and R is a non-hydrogen substituent.

23. A method for preparing an onium salt compound, the method comprising:
(a) providing an onium salt compound comprising a sulfonate component, wherein the sulfonate component comprises an electron withdrawing group;
(b) treating the onium salt compound with a halide salt to permit displacement of the sulfonate component with the halide salt anion to provide a distinct salt of the onium compound;
(c) admixing the distinct salt of the onium compound with a polymer to provide a photoresist composition.

* * * * *